United States Patent [19]

Stewart et al.

[11] Patent Number: 4,983,529

[45] Date of Patent: * Jan. 8, 1991

[54] IMMUNOASSAY FOR HIV-I ANTIGENS USING F(AB')₂ FRAGMENTS AS PROBE

[75] Inventors: James L. Stewart, Buffalo Grove; Susan K. Ketchum, Libertyville; Robert J. Stumpf, Chicago, all of Ill.

[73] Assignee: Abbott Laboratories, Abbott Park, Ill.

[ * ] Notice: The portion of the term of this patent subsequent to May 31, 2005 has been disclaimed.

[21] Appl. No.: 204,799

[22] Filed: Jun. 10, 1988

[51] Int. Cl.⁵ .................. G01N 33/563; C12Q 1/70; C12Q 1/00

[52] U.S. Cl. .................................. 436/512; 435/5; 435/7; 436/511; 436/513

[58] Field of Search .............. 435/5, 7; 436/811, 8 B

[56] References Cited

U.S. PATENT DOCUMENTS

| | | | |
|---|---|---|---|
| 4,200,436 | 4/1980 | Mochida et al. | 23/230 |
| 4,292,403 | 9/1981 | Duermeyer | 435/5 |
| 4,298,593 | 11/1981 | Ling | 424/1 |
| 4,722,893 | 2/1988 | Shigeta et al. | 435/7 |
| 4,732,848 | 3/1988 | Lenz et al. | 435/7 |
| 4,748,110 | 5/1988 | Paul . | |

FOREIGN PATENT DOCUMENTS

| | | |
|---|---|---|
| 8660074 | 1/1987 | Australia . |
| 8473 | 3/1980 | European Pat. Off. . |
| 173375 | 3/1986 | European Pat. Off. . |

OTHER PUBLICATIONS

P. Tijssen in: Practice and Theory of Enzyme Immunoassays, General Edits by Burdon & Knippenberg, Elsevier, 1985, pp. 117–119, 373–375.

Yolken, R. H. et al., "Enzyme Immunoassays for the Diagnosis of Viral Infections in: Defined Immunofluorescence & Related Cytochemical Methods Annals of the N.Y. Acad. Sci.", vol. 420: 381–390.

Primary Examiner—Robert A. Wax
Assistant Examiner—Bradley L. Sisson
Attorney, Agent, or Firm—Judith A. Woods

[57] ABSTRACT

The present invention provides a probe for the detection of HIV 1 antigens, comprising anti-HIV 1 F(Ab')₂ fragments. The invention further provides an immunoassay with enhanced specificity.

14 Claims, No Drawings

IMMUNOASSAY FOR HIV-I ANTIGENS USING F(AB')₂ FRAGMENTS AS PROBE

BACKGROUND OF THE INVENTION

The present invention relates to the detection of the Human Immunodeficiency Virus (HIV) in serum, plasma or other body fluids. In particular, this invention describes diagnostic assays which employ $F(ab')_2$ fragments as a probe for the detection of HIV 1 antigens.

HIV 1 is believed to be the causative agent in acquired immunodeficiency syndrome (AIDS) [Chamberland et al., *Ann. Int. Med.* (1984) 101:617–623; Seligman et al., *New Eng. J. Med.* (1984) 311:1286–1292]. The virus has been isolated from patients with AIDS and AIDS-related complex (ARC) as well as from healthy persons at high risk for AIDS (Gallo et al., *Science* (1984) 244:500–502).

Since Dec. 1986, enzyme immunoassays, for example, the Abbott HIV 1 Antigen assay (Abbott Laboratories, North Chicago, Illinois), have been commercially available on a research basis for detection of HIV 1 antigens. These tests are highly sensitive and provide a direct indication of the presence of the virus. Consequently, detection of HIV 1 antigens may be useful as an aid in the diagnosis and monitoring of HIV 1 infection (Pedersen et al., *Brit. Med. J.* (1987) 295:567–569; DeWolf et al., *Brit. Med. J.* (1987) 295:569–572).

The sensitivities of the current HIV 1 antigen assays are quite good, however, the specificity varies widely. All manufacturers appear to have samples which nonspecifically react with components of the assay yielding false reactives. For this reason, Abbott provides a confirmatory procedure which involves neutralization of HIV 1 antigen in the sample prior to assaying. Although this increases specificity to near 100%, the cost involved in additional testing warrants efforts to increase the predictive value of antigen testing. The invention described herein provides one method of significantly increasing specificity while also enhancing assay sensitivity and timing.

SUMMARY OF THE INVENTION

A probe for the detection of HIV 1 antigens in plasma, serum, tissue culture and other biological fluids is provided by the present invention. This probe is a chemically modified antibody. The modification involves enzymic cleavage of antibodies to HIV 1 to produce $F(ab')_2$ fragments.

Highly specific diagnostic assays to detect HIV 1 antigens, using a $F(ab')_2$ probe, are provided by the invention. When used in conjunction with labeled $F(ab')_2$ fragments specific for the $F(ab')_2$ probe described above, an assay of the invention is capable of detecting HIV 1 antigen with greater specificity and sensitivity than previously observed. Immunoassays of the invention comprise:

(1) coating a solid support with anti-HIV 1 antibody;
(2) contacting the solid support with a biological sample;
(3) contacting the solid support with a probe comprising anti-HIV 1 $F(ab')_2$ fragments from a different animal species than that used in step 1;
(4) contacting the solid support with $F(ab')_2$ fragments specific for the probe used in step 3 conjugated to a label; and
(5) detecting the label as a measure of the presence of HIV 1 antigen in the sample.

In an especially preferred assay of the invention, monoclonal antibodies, most preferably those designated 31-42-19 and 31-90-25, are coated on the solid support to specifically capture HIV 1 p24 antigens.

DETAILED DESCRIPTION

The present invention provides an improved means for the detection of HIV 1 antigens. The use of $F(ab')_2$ fragments as a probe in an immunoassay to detect HIV 1 antigens increases assay specificity while at the same time enhances assay sensitivity. For example, this probe can be utilized advantageously to improve the immunoassay disclosed in U.S. Pat. No. 4,748,110, issued May 31, 1988.

Alternately, any antigen binding fragment, such as Fab monomers, produced by cleavage of anti-HIV 1 antibodies with the enzyme papain, can be employed as a probe in the inventive assays.

In addition to using anti-HIV 1 $F(ab')_2$ fragments as a probe, $F(ab')_2$ fragments specific for the probe can be labeled and used to measure the amount of HIV 1 antigen present in the sample. Any label capable of producing a detectable signal can be used in the assays of the invention. Representative labels include enzymes, radioisotopes, fluorescent and chemiluminescent labels. Further, hapten/labeled anti-hapten systems such as a biotin/labeled anti-biotin system can be utilized in the inventive assays.

Both polyclonal and monoclonal antibodies are useful as reagents to capture HIV 1 antigen on the solid support used in an assay of the invention. In an especially preferred embodiment of the invention, mouse monoclonal antibodies to HIV 1 p24 designated 31-42-19 and 31-90-25, disclosed in an U.S. application, entitled "Mouse Monoclonal Antibodies to HIV 1 p24 and Their Use in Diagnostic Tests," filed by S. Mehta et al. concurrently with this application and deposited at the ATCC, Rockville, Maryland under accession numbers HB 9726 and HB 9725, respectively, are utilized to specifically capture HIV 1 p24 antigen. In addition, both IgG and IgM antibodies may be used in the assays of the invention.

Biological samples which are easily tested by the method of the present invention include human and animal body fluids such as whole blood, serum, plasma, cerebrospinal fluid and lymphocyte or cell culture supernatants. Solid supports which can be used in immunoassays of the invention include wells of reaction trays, test tubes, polystyrene beads, strips membranes, microparticles and other solid matrices known to those skilled in the art.

In addition, reagents for the assays of the invention are ideally suited for preparation of a kit. Such a kit may comprise carrier means being compartmentalized to receive in close confinement, one or more container means such as vials, bottles, test tubes and the like. Each of the container means comprises one of the separate elements to be used in the assay.

Current immunoassays for detecting HIV 1 have limited specificity in that they routinely detect as reactive, or positive, samples which have no HIV 1 antigens. These false positives are caused, in large part, by nonspecific reactions of the antibodies used with interfering substances (for example, rheumatoid factor). These reactions are often mediated by the Fc portions of the antibody molecules. By utilizing $F(ab')_2$ fragments, one can eliminate most of these nonspecific interactions. The enhanced specificity afforded by the F(ab')$_2$ fragments greatly increases the utility of the assays of the present invention in the diagnosis and monitoring of patients infected with HIV 1. The following examples illustrate other advantages of the invention.

EXAMPLE 1

Preparation of F(ab')$_2$ Fragments

Rabbit anti-HIV 1 antibodies were subjected to cleavage with pepsin according to standard procedures (Fanger et al., *J. Immunol.* (1970) 105:1484–1492; Parham, *J. Immunol.* (1983) 131:2895–2902). The F(ab')$_2$ fragments were isolated from the digestion mixture by gel filtration chromatography. Analysis by sodium dodecyl sulfate polyacrylamide gel electrophoresis (Laemmli, *Nature* (1970) 227:680–685) confirmed the presence of intact F(ab')$_2$ fragments. This product retains the specificity for recognizing HIV 1 proteins, while eliminating the nonspecific reactions frequently mediated by the Fc portion of the whole molecule antibody.

EXAMPLE 2

F(ab')$_2$ Fragments Used as Probe in Enzyme Immunoassay (EIA) for Detection of HIV 1 Antigens A representative assay of the invention is described below:

(1) A human polyclonal anti-HIV 1 IgG coated ¼ inch polystyrene bead was contacted with 200 μl of plasma, serum or other biological fluid. After an overnight incubation (16–20 hours) at room temperature, the bead was washed three times with 5 ml water to remove unbound sample.

(2) The washed bead was contacted with 200 μl of rabbit F(ab')$_2$ anti-HIV 1 and incubated for 1 hour at 40° C. in a waterbath. The bead was then washed as described in step 1 to remove unbound reagent.

(3) The washed bead was contacted with 200 μl of goat F(ab')$_2$ anti-rabbit F(ab')$_2$ conjugated to horseradish peroxidase (HRPO) [Pel-Freeze Biologicals, Rogers, Arkansas], and incubated for 2 hours at 40° C. in a waterbath. The bead was washed again as described in step 1.

(4) The washed bead was contacted with 300 μl of o-phenylenediamine-hydrogen peroxide solution, at room temperature for approximately 30 minutes, which formed a yellow-orange colored product in the presence of horseradish peroxidase. The reaction was quenched with 1N H$_2$SO$_4$; then, absorbance was read at 492 nm.

Alternately, steps 2 and 3 may be combined into one step to facilitate the procedure. Species of antibodies other than human can be used to capture the HIV 1 antigens, and species of F(ab')$_2$ fragments other than rabbit also can be used as the probe. Better specificity is achieved when the capture and probe antibodies are from different animal species. F(ab')$_2$ fragments also can be used to coat the beads, in addition to its use as the probe and the conjugate.

Additionally, shorter incubation times are possible by incubating the reaction mixtures at 40° C. in a waterbath or in a dynamic incubator. For example, in the above-described assay, the incubation times of sample, anti-HIV 1 F(ab')$_2$ fragments, and conjugate can be reduced to 1.5 hours, 0.5 hours and 2 hours, respectively, when incubations take place at 40° C. in a waterbath.

EXAMPLE 3

The specificity of the assay described in Example 2 was determined using eight nonspecific samples. These samples are repeatably reactive but nonconfirming in the Abbott HIV 1 Antigens assay. This assay uses whole molecule antibodies as a probe. For both assays, an absorbance value which was 0.05 O.D. units greater than that of the negative control was considered the cutoff value. Samples showing higher absorbance values than the cutoff value were considered reactive for HIV 1 antigens. Therefore, samples having a sample to cutoff absorbance value (S/C) greater than or equal to 1.0 were considered reactive. All reactive samples were tested by the Abbott HIV 1 neutralization test, commercially available from Abbott Laboratories for research use. A sample which was neutralized by the procedure was considered to be confirmed positive for HIV 1 antigens.

The data provided in Table 1 shows that all eight specimens were negative using two different production lots of rabbit F(ab')$_2$ fragments as the probe.

TABLE 1

| | Comparative Profile of Nonspecific Samples. | | |
|---|---|---|---|
| | Sample to Cutoff Value | | |
| Sample Number | Abbott HIV 1 Ags Assay | F(ab')$_2$ Lot #1 | F(ab')$_2$ Lot #2 |
| 1 | 1.328 | 0.502 | 0.420 |
| 2 | 1.670 | 0.742 | 0.735 |
| 3 | 1.233 | 0.459 | 0.378 |
| 4 | 3.226 | 0.469 | 0.420 |
| 5 | 1.044 | 0.404 | 0.389 |
| 6 | 4.934 | 0.426 | 0.452 |
| 7 | 6.641 | 0.480 | 0.504 |
| 8 | 1.452 | 0.448 | 0.410 |

EXAMPLE 4

To analyze the assay sensitivity, defined as picograms of HIV 1 p24 per ml that gave an absorbance value equal to the cutoff value, a serial dilution panel of purified HIV 1 p24 antigen was assayed, and the sensitivity determined by linear regression. The signal to noise ratio (S/N), defined as the ratio of the positive control absorbance value mean to the negative control absorbance value mean, also was compared.

The experiment, results of which are shown in Table 2, compared the performance of the F(ab')$_2$ probe assay, using either human polyclonal anti-HIV 1 IgG (the same as that in the Abbott HIV 1 Antigens assay) or mouse monoclonal anti-HIV 1 IgG (the monoclonal antibodies designated 31-42-19 and 31-90-25) on the solid support. Assay sensitivities were measured using a standard procedure for all three assays, with incubation times of 16–20 hours, 4 hours and 2 hours, respectively, for sample, anti-HIV 1 probe and conjugate. In both assays where F(ab')$_2$ fragments were used, the signal to noise ratio increased, and the detectability of HIV 1 antigen improved significantly. In particular, when the F(ab')$_2$ probe was used in conjunction with the monoclonal antibodies, the sensitivity was less than 1 pg/ml.

TABLE 2

| | Mean Positive Control | S/N | Sensitivity (pg p24/ml) |
|---|---|---|---|
| Abbott HIV 1 Antigens Assay | 1.342 | 30.5 | 5.1 |

TABLE 2-continued

|  | Mean Positive Control | S/N | Sensitivity (pg p24/ml) |
|---|---|---|---|
| F(ab')2 Probe (Human IgG Capture) | 2.444 | 37.6 | 2.2 |
| F(ab')2 Probe (Monoclonal IgG Capture) | 2.896 | 36.6 | 0.6 |

Sensitivity was also compared on a panel of HIV 1 antigen positive specimens consisting of neat and diluted samples from six different HIV 1 antigen positive donors. The same beads, coated with human anti-HIV 1 IgG were used for both assays. The results, illustrated in Table 3, show that the F(ab')2 probe assay, was capable of detecting 23 out of 29 samples as positive, as compared to 16 out of 29 for the Abbott HIV 1 antigens assay.

TABLE 3

| | | Sample to Cutoff Value | |
|---|---|---|---|
| Donor | Member | Abbott HIV 1 Antigen Assay | F(ab')2 Assay |
| 1 | A | 1.56 | 2.95 |
|   | B | 1.26 | 2.02 |
|   | C | 1.08 | 1.48 |
|   | D | 0.75 | 1.02 |
|   | E | 0.62 | 0.74 |
| 2 | A | 1.89 | 2.26 |
|   | B | 1.15 | 1.65 |
|   | C | 0.92 | 1.24 |
|   | D | 0.66 | 0.92 |
|   | E | 0.60 | 0.57 |
| 3 | A | 2.90 | 6.73 |
|   | B | 1.89 | 3.86 |
|   | C | 1.37 | 2.24 |
|   | D | 0.89 | 1.30 |
|   | E | 0.65 | 0.87 |
| 4 | A | 4.19 | 5.57 |
|   | B | 3.76 | 5.73 |
|   | C | 3.26 | 4.31 |
|   | D | 2.46 | 3.50 |
|   | E | 1.96 | 2.49 |
|   | F | 1.73 | 1.73 |
|   | G | 0.89 | 1.02 |
|   | H | 0.50 | 0.68 |
| 5 | A | 1.02 | 1.82 |
|   | B | 0.88 | 1.29 |
|   | C | 0.50 | 0.35 |
| 6 | A | 1.53 | 2.18 |
|   | B | 0.98 | 1.65 |
|   | C | 0.79 | 1.20 |
| Total Positive | | 16 | 23 |

Because of the enhanced signals and sensitivity obtained with F(ab')2 fragments, it is possible to significantly shorten the time required to assay specimens. Several short configurations have been employed, including one assay of 3.5 hours, with incubation times of 1 hour each, at 40° C., for antigen capture on solid support by monoclonal anti-HIV 1, incubation of solid support with rabbit F(ab')2 anti-HIV 1 and incubation of solid support with goat F(ab')2 anti-rabbit F(ab')2, followed by color development with o-phenylenediamine. Despite eliminating over 20 hours of incubation time, the calculated sensitivity for this procedure was 2.7 pg p24/ml.

While specific examples have been given to illustrate the invention, it is to be understood that those skilled in the art will recognize variations without departing from the spirit and scope of the invention.

What is claimed is:

1. An immunoassay for the detection of HIV 1 antigens in a biological sample comprising forming an antibody/antigen complex wherein the antibody portion of said complex comprises anti-HIV 1 F(ab')2 fragments, and detecting the presence or amount of the antibody/antigen complex formed.

2. The immunoassay of claim 1 wherein the presence or amount of the antibody/antigen complex formed is determined by incubating said complex with a labeled, anti-species antibody specific for said anti-HIV 1 fragments.

3. The immunoassay of claim 2 wherein said anti-species antibody comprises F(ab')2 fragments.

4. The immunoassay of claims 2 or 3 wherein said label comprises a radioisotope, enzyme, fluorescent compound, chemiluminescent compound, or member of a specific binding pair.

5. The immunoassay of claim 3 wherein said antibody portion of said complex further comprises anti-HIV 1 antibody bound on a solid support.

6. The immunoassay of claim 5 wherein said bound anti-HIV 1 antibody comprises at least one monoclonal antibody.

7. The immunoassay of claim 6 wherein said bound anti-HIV 1 antibody comprises the monoclonal antibodies designated 31-42-19 and 31-90-25 deposited at the ATCC under accession numbers HB 9726 and HB 9725, respectively.

8. The immunoassay of claim 5 wherein said bound anti-HIV 1 antibody comprises a polyclonal anti-HIV 1.

9. The immunoassay of claims 6, 7 or 8 wherein said bound antibody further comprises F(ab')2 fragments.

10. An immunoassay for the detection of HIV 1 p24 antigen in a biological sample comprising the steps of:
 a. coating a solid support with a monoclonal antibody mixture derived from a first animal species;
 b. contacting the coated support with the sample, incubating and washing;
 c. contacting the support with a probe comprising anti-HIV 1 F(ab')2 fragments from a second animal species, incubating and washing;
 d. contacting the support with labeled F(ab')2 fragments specific for said probe, incubating and washing;
 e. contacting the support with an o-phenylenediamine-hydrogen peroxide solution; and
 f. measuring the absorbance of the color product formed at 492 nm to determine the presence of HIV 1 p24 in the sample;
wherein said monoclonal antibody mixture comprises the monoclonal antibodies designated 31-42-19 and 31-90-25 deposited at the ATCC under accession numbers HB 9726 and HB 9725, respectively.

11. An immunoassay for the detection of HIV 1 antigens in a biological sample comprising the steps of:
 a. coating a solid support with anti-HIV 1 antibody from a first animal species;
 b. contacting the coated support with the sample, incubating and washing;
 c. contacting the support with a probe comprising anti-HIV 1 F(ab')2 fragments from a second animal species, incubating and washing;
 d. contacting the support with labeled F(ab')2 fragments specific for said probe, incubating and washing;
 e. contacting the support with an o-phenylenediamine-hydrogen peroxide solution; and f. measuring the absorbance of the color product formed at 492 nm to determine the presence of HIV 1 antigens in the sample.

12. A dignostic reagent for the detection of HIV 1 antigens comprising anti-HIV 1 F(ab')$_2$ fragments.

13. A diagnostic kit for the detection of HIV 1 antigens comprising the diagnostic reagent of claim 12.

14. A diagnostic kit for the detection of HIV 1 p24 antigen comprising anti-HIV 1 F(ab')$_2$ fragments and the monoclonal antibodies designated 31-42-19 and 31-90-25 deposited at the ATCC under accession numbers HB 9726 and HB 9725, respectively.

* * * * *